(12) United States Patent  (10) Patent No.: US 7,875,857 B2
Barnard  (45) Date of Patent: Jan. 25, 2011

(54) X-RAY PHOTOELECTRON SPECTROSCOPY ANALYSIS SYSTEM FOR SURFACE ANALYSIS AND METHOD THEREFOR

(75) Inventor: Bryan Robert Barnard, Nutley (GB)

(73) Assignee: Thermo Fisher Scientific Inc., Waltham, MA (US)

( * ) Notice: Subject to any disclaimer, the term of this patent is extended or adjusted under 35 U.S.C. 154(b) by 315 days.

(21) Appl. No.: 11/866,489

(22) Filed: Oct. 3, 2007

(65) Prior Publication Data

US 2008/0142707 A1   Jun. 19, 2008

(30) Foreign Application Priority Data

Oct. 3, 2006 (GB) ................................ 0619518.4

(51) Int. Cl.
*H01J 47/00* (2006.01)
*H01J 49/00* (2006.01)
*G21K 1/06* (2006.01)

(52) U.S. Cl. ........................... 250/396 R; 250/396 ML; 250/398; 378/138; 378/119; 378/113; 378/101; 378/84

(58) Field of Classification Search ............. 250/396 R, 250/396 ML, 398; 378/119, 113, 101, 138, 378/84
See application file for complete search history.

(56) References Cited

U.S. PATENT DOCUMENTS

| | | | |
|---|---|---|---|
| 3,471,694 A | 10/1969 | Poen | |
| 3,679,927 A | 7/1972 | Kirkendall | |
| 5,072,125 A | 12/1991 | Nakanishi et al. | |
| 5,128,977 A | 7/1992 | Danos | |
| 5,206,895 A | 4/1993 | Danos | |
| 5,511,104 A | 4/1996 | Mueller et al. | |
| 5,689,541 A * | 11/1997 | Schardt | 378/140 |
| 5,987,097 A | 11/1999 | Salasoo | |
| 2002/0040970 A1* | 4/2002 | Lee et al. | 250/492.2 |

(Continued)

FOREIGN PATENT DOCUMENTS

EP    0143495    11/1983

(Continued)

OTHER PUBLICATIONS

Great Britain Search Report for GB0619518.4 dated Feb. 12, 2007.

(Continued)

*Primary Examiner*—Nikita Wells
(74) *Attorney, Agent, or Firm*—Haynes and Boone LLP (57) ABSTRACT

An X-ray photoelectron spectroscopy analysis system for analysing an insulating sample 20, and a method of XPS analysis. The system comprises an X-ray generating means 30 having an exit opening 32 and being arranged to generate primary X-rays 46,56 which pass out of the exit opening in a sample direction towards a sample surface 22 for irradiation thereof. It has been found that the X-ray generating means in use additionally generates unwanted electrons 258 which may pass out of the exit opening substantially in the sample direction and cause undesirable sample charging effects. The system further comprises an electron deflection field generating means 380,480,580 arranged to generate a deflection field upstream of the sample surface. The deflection field is configured to deflect the unwanted electrons away from the sample direction, such that the unwanted electrons are prevented from reaching the sample surface.

24 Claims, 5 Drawing Sheets

U.S. PATENT DOCUMENTS

2002/0064253 A1* 5/2002 Gutman .................. 378/84

FOREIGN PATENT DOCUMENTS

| GB | 1136255 | 12/1968 |
| GB | 1493767 | 11/1977 |
| GB | 2411763 A | 9/2005 |
| JP | 2006085927 | 3/2006 |
| WO | 0219377 A2 | 3/2002 |

OTHER PUBLICATIONS

European Search Report for GB0619518.4 dated Oct. 3, 2006.

Larson, Paul E. et al., "Surface Charge Neutralization of Insulating Samples in X-Ray Photoemission Spectroscopy", J. Vac. Sci. Technol. A 16(6), Nov./Dec. 1998, pp. 3483-3489.

UK Search and Examination Report dated Feb. 13, 2007, Application No. GB0619518.4, 7 pages.

European Patent Office, Search Report dated Feb. 6, 2008, Application No. 07253909.1-1240, 6 pages.

Response to EP Search Report dated Feb. 6, 2008, and filed Oct. 9, 2008, Application No. 07253909.1, 17 pages.

Response to UK Search Report dated Feb. 13, 2007, and filed Oct. 3, 2008, Application No. GB0619518.1, 35 pages.

* cited by examiner

Fig. 5 ions etc.) emitted from the surface as a result. Control of the electric potential of the sample surface is important, to ensure accurate measurements can be taken.
X-RAY PHOTOELECTRON SPECTROSCOPY ANALYSIS SYSTEM FOR SURFACE ANALYSIS AND METHOD THEREFOR

CROSS REFERENCE

This application claims priority benefit of Great Britain Patent Application Number 0619518.4, filed Oct. 3, 2006.

FIELD OF THE INVENTION

The invention relates to an X-ray photoelectron spectroscopy (XPS) analysis system suitable for analysing an insulating sample, and an XPS analysis method.

BACKGROUND OF THE INVENTION

Surface analysis for materials characterisation involves directing a beam of primary particles (photons, electrons, ions etc.) to the surface of a sample and measuring the energy or mass of the secondary particles (photons, electrons, ions etc.) emitted from the surface as a result. Control of the electric potential of the sample surface is important, to ensure accurate measurements can be taken.

In monochromated XPS analysis, a primary beam of monochromatic X-ray photons causes the emission of secondary electrons from the sample surface. For an insulating sample (such as an insulator, an electrically isolated conductive sample, a conductive sample with an insulating surface, or a sample including one or more electrically isolated regions), the emission of secondary electrons leaves the analysis region positively charged. It is known to use an electron flood gun to provide charge compensation for the electrons emitted from the sample surface. The purpose of the flood gun is to charge the surface to a negative potential, approximately equivalent to the energy of the incident electrons in the flood, so that a dynamic steady state is set up, in which flood electrons reach the sample surface at the same rate as the secondary electrons leaving the surface and any excess flood electrons are reflected from the surface.

In practice, however, a uniform surface potential is not provided. Any areas of the sample surface which are not irradiated by X-rays, but receive incident electrons, become charged to the potential of the most energetic incident electrons. These areas then act to repel flood electrons which are needed to replace the photoemitted electrons from the analysis region which is irradiated by X-rays. The net negative charge developed around the irradiated, analysis region also acts to defocus the electron beam from the flood gun. These effects are particularly severe when the sample is much larger than the analysis region.

It is known to use a beam of low-energy, positive ions to neutralise this build-up of negative charge.

Larson and Kelly, "Surface charge neutralisation of insulating samples in X-ray photoemission spectroscopy", Journal of Vacuum Science and Technology A, 16(6), November/December 1998, pp 3483-3489, indicate that the principal cause of the negative potential in the region surrounding the analysis region is the energy spread of the flood electrons from the electron flood gun, which includes a high-energy tail. Larson and Kelly use a neutralising system in which a high current density flood gun with a narrow energy spread is used in combination with a source of low-energy, positive ions.

GB-A-2,411,763 provides a background discussion of the above problem and discloses a combined flood gun, which provides a source of electrons and a source of positively charged particles and is capable of focusing the electron flood beam and the positive particle beam independently towards the sample surface. Although the combined flood gun of GB-A-2,411,763 provides an effective instrument for neutralising the unwanted electrons at the sample surface, facilitating further the control of the potential of the sample surface would be desirable. The invention aims to address the above and other objectives by providing an improved XPS analysis system for surface analysis.

SUMMARY OF THE INVENTION

According to one aspect of the invention, there is provided an X-ray photoelectron spectroscopy analysis system for analysing an insulating sample, the system comprising: an X-ray generating means having an exit opening and being arranged to generate primary X-rays which pass out of the exit opening in a sample direction towards a sample surface for irradiation thereof, the X-ray generating means in use additionally generating unwanted electrons which would pass out of the exit opening substantially in the sample direction; and an electron deflection field generating means arranged to generate a deflection field upstream of the sample surface, the deflection field being configured to deflect the unwanted electrons away from the sample direction, such that the unwanted electrons are prevented from reaching the sample surface.

The present inventor has established that a significantly more troublesome source of energetic incident electrons is the X-ray monochromator itself. That is, the electrons from the X-ray monochromator have a more significant effect on the negative potential on the sample surface than the flood electrons in the high-energy tail of the energy distribution from the electron flood gun. Careful measurements have demonstrated that, even though there is no direct line of sight from the X-ray source in the X-ray monochromator to the sample surface, there is a sufficient number of electrons generated in the X-ray monochromator to cause significant charging of the sample surface.

It is understood that these electrons result from a) scattering from the walls of the monochromator chamber and from the monochromator crystal by high-energy electrons from the electron gun used to generate X-rays at the X-ray source; b) X-ray photoelectron emission from the walls of the monochromator chamber and from the monochromator crystal and its mount, excited by both the Al (aluminium) K-alpha X-rays and the Bremsstrahlung radiation from the X-ray source; and c) secondary and higher-order electrons generated by both of the processes (a) and (b) and by electron bombardment of the target anode in the X-ray source.

It has been established that, while the electron currents of the above incident electrons may be relatively small—perhaps in the region of a few hundred picoamps reaching the sample surface—the electrons may nevertheless cover a wide energy range. In principle, the energy of such an electron may be up to the energy of the X-ray source electron beam from the electron gun, which is typically 15 kV, but the electron energy is normally up to a few tens of electron volts. So, despite being a comparatively small current, the electrons from the X-ray generating means can have a much higher energy than flood electrons from a flood gun and, by charging the surface of the sample over a large area to a large negative potential, can prevent the flood electrons from ever reaching the analysis area.

Initial attempts by the inventor to remove the unwanted electrons from the X-ray monochromator involved the use of an X-ray window at the exit port of the X-ray monochromator.

The window was made from ultra-thin aluminium or polymer, with a high transmission of around 90% at the aluminium K-alpha X-ray wavelength, to achieve effective blocking of unwanted electrons from the X-ray source. However, the inventor found that, because typically 10% of the X-rays passing from the monochromator to the source were absorbed by the window, further unwanted electrons were generated by this process and could reach the sample with high energy, so that the net unwanted electron current at the sample surface was not significantly reduced through use of the window.

As a result of further investigations, the inventor has established that an effective technique for addressing the problem of energetic incident electrons is to apply a deflection field across the pathway of the unwanted electrons upstream of the sample surface. The deflection field is arranged to deflect the unwanted electrons away from their trajectory to the sample surface, such that the unwanted electrons are prevented from reaching the surface. As a result of the deflection field applied to the unwanted electrons, the unwanted electrons are diverted away from their path and allowed to hit other components in the analysis system, such as the analysis chamber sidewall. The deflection field is arranged to be of sufficient strength to deflect high-energy, as well as low-energy, unwanted electrons away from the sample surface. The deflection field has no effect on the desired primary X-rays travelling towards the sample surface, so that primary beam irradiation of the surface may continue as normal.

In this way, embodiments of the invention are able to provide a reduction by more than a factor of ten in the unwanted electron current reaching the sample surface. Consequently, where a charge neutralisation system is employed (as described in GB-A-2,411,763 or by any other means), the positive ion beam generated by the charge neutralisation system to compensate for the arrival of energetic incident electrons at the sample surface may be reduced in current, in correspondence with the reduction of the unwanted electron current. This results in a reduction in sample damage caused by the positive ion beam. Furthermore, with a reduction in the positive ion beam current required by the charge neutralisation system, the amount of gas which is to be ionised for providing the ion beam may be significantly reduced. A reduction in the amount of gas, which is typically argon, which needs to be admitted to the charge neutralisation system and the analysis chamber leads to a reduction in contamination in the system. Overall, the performance of the charge neutralisation system may be enhanced by improved ease of use, in view of the above benefits, especially for large samples where the ion beam techniques above have limited efficacy.

The invention relates to an X-ray photoelectron spectroscopy apparatus and method, which aim to address in particular the undesirable surface-charging problem encountered when analysing the surface of an insulating sample. A significant cause of the problem was identified by the inventor as being electrons generated in the X-ray generator. The inventor addressed this problem by applying a deflection field across the pathway of the unwanted electrons upstream of the sample surface.

X-ray generators are known from many different technical fields. It is to be noted that many prior art X-ray generators would not be suitable for XPS surface analysis of a sample, in view of their operational or structural configurations.

X-ray generators for XPS analysis of samples are generally low-power, typically of a few hundred watts; low-energy, typically electron energies up to 15 kV; produce very soft X-rays, typically with an energy of 1.5 kV (expressed in the same terms as electron energies); and are generally designed for continuous operation, without a vacuum window between the X-ray source and the sample.

X-ray generators used in medical applications, for example, are generally high-power, typically several kilowatts; very high-energy, typically electron energies above 50 kV; produce hard X-rays, typically above 10 kV; and operate for only short periods. Other X-ray generators, which are set for such high-energy operation, find application in X-ray diffraction or X-ray imaging. As indicated above, such high-energy X-ray generators are unsuitable for XPS sample surface analysis, since the hard X-rays generated would not interact with atoms at the sample surface, but would penetrate deep within the sample.

A number of prior art X-ray generators are configured as a sealed tube, with an X-ray-transmissive vacuum window, which is arranged to withstand atmospheric pressure. The soft (aluminium K-alpha) X-rays generally used for XPS surface analysis are of such low energy that sealed tubes with X-ray windows which are thick enough to support atmospheric pressure are not suitable, since they will effectively not transmit such X-rays. Indeed, some X-ray generators specifically take advantage of this effect; in particular in X-ray diffraction arrangements, where it is desirable to have only a single, characteristic, hard X-ray irradiating beam (so it is beneficial to filter out any characteristic, soft X-rays). It may be possible to employ a very thin window (typically of aluminium) with a soft X-ray source for sample surface analysis, but such a window could not be made thick enough to sustain an atmospheric pressure difference. Indeed, as mentioned above, the use of such a window can itself generate secondary electrons, which has a detrimental effect on the surface-charging problem identified in the application.

A number of high-energy X-ray generators suffer from the problems of the X-ray window becoming hot or patient tissue becoming damaged, from very high-energy electrons produced in the X-ray generators. Neither of these problems is relevant for X-ray generators suitable for XPS sample surface analysis. Furthermore, such problems in a high-energy X-ray generator may be dealt with by reducing the electron beam in the X-ray generator down to the milliamp or microamp level. Electrons with energies below a few hundred volts would be of little interest, since they would cause no significant patient tissue damage or window heating (indeed, their path length in air would generally be too short to reach the patient). In XPS sample surface analysis, it is desirable to reduce the electron beam reaching the sample surface down to below the nanoamp level. In addition, it has been recognised by the inventor that it is precisely those electrons of energies in the range of a few volts to a hundred volts which cause most of the surface-charging effects.

In high-energy X-ray generators, high-energy electrons may be deflected away from the window or the patient, but eventually they must hit the wall of the chamber somewhere, at which point they will typically produce a large quantity of lower-energy, secondary electrons. If the X-ray generator has a sealed window, these secondary electrons may or may not escape, depending on their energy, but in any case they will have lost enough energy no longer to be a problem in medical applications, say. They would, however, still have enough energy to cause surface charging in an XPS system. If the X-ray generator does not have a window, as would be the case generally for XPS, using soft X-rays, then a large fraction of these lower-energy, secondary electrons would certainly escape and cause surface-charging effects.

This invention lies in the field of XPS analysis. Prior art X-ray generators used in XPS analysis are configured specifically to this field. The surface-charging problem caused by the unwanted electrons generated in XPS X-ray generators was not recognised in the prior art. The recognition by the inventor of this problem has led to the modification of an X-ray generator as used for XPS analysis.

Preferably, the deflection field generating means is located near to, at, or upstream of the exit opening. That is, the deflection field generating means may be located outside of the X-ray generating means, but near to its exit opening; or it may be around or adjacent the exit opening; or it may be located on the X-ray generating means side of the exit opening. It is preferable for the electron deflection field to be generated in the region of the exit opening, in this way, since the unwanted electrons may then be dealt with before, or as, they pass out of the exit opening. This provides a relatively large distance over which the deflected unwanted electrons may travel so as to avoid the sample surface. Preferably, the unwanted electrons are deflected so that they are received by the sidewalls of an analysis chamber holding the sample.

Preferably, the deflection field is transverse to the sample direction. This has the benefit of providing the largest deflecting force on the unwanted electrons for a given field strength.

Preferably, the X-ray generating means has a housing portion terminating in the exit opening. The deflection field generating means may be located internally of the housing portion; that is, within the arm, or flight tube, heading towards the exit opening of the X-ray generating means. This provides a reasonable separation between the deflection field generating means and the sample, so that any field at the sample surface is acceptably low. Alternatively, the deflection field generating means may be located externally of the housing portion; that is, on the outside of the arm, or flight tube, of the X-ray generating means heading towards the exit opening. This facilitates access to the deflection field generating means for repair or removal, for example, during bake-out of the system. In addition, this facilitates the configuration and operation of the deflection field generating means if this is provided by an electromagnet.

Preferably, the system comprises an analysis chamber for holding the sample. The chamber comprises a sidewall having an entrance port therethrough in communication with the exit opening of the X-ray generating means, to allow X-rays to pass from the generating means to the sample surface. In a preferred embodiment, the deflection field generating means is located in this port. This ensures that the deflection field acts on all of the unwanted electrons which have been generated in the X-ray generating means and which have passed out of the exit opening.

The inventor has found that best results are achieved when the deflection field generating means is positioned outside or within this chamber sidewall, since this helps to ensure that the deflecting field inside the chamber is acceptably low. The currently preferred position is near to the port where the X-rays pass through the chamber sidewall, as the beam is generally narrow here and the volume through which the deflection field is required to act is relatively small.

The electron deflection field may be magnetic and may be provided using an electromagnet. This provides the possibility of controlling the magnetic field strength during operation. Preferably, however, the deflection field generator comprises a permanent magnet. This provides a simple and effective mechanism for deflecting the unwanted electrons, since once the permanent magnet is positioned in place no further configuration or control of it is required.

The deflection field generator may be arranged to produce a local magnetic field of between 1 mT and 100 mT. Preferably, the local magnetic field is between 10 mT and 50 mT. The inventor has found that such a magnetic field is effective to stop all high-energy unwanted electrons.

Preferably, at least the part of the chamber sidewall comprising the entrance port is made of a magnetic material, such as soft iron or preferably a nickel-iron alloy. In this way, it may be configured to act as a flux return path for the magnetic field. Furthermore, the chamber sidewall made of such a magnetic material may be used to provide magnetic shielding of the sample surface from the deflection field. Preferably, the chamber sidewall is sufficiently thick that the magnetic field applied by the deflection field generator does not saturate the sidewall material and the shielding factor remains high. The inventor has in this way been able to achieve a low field at the sample, of less than $10^{-6}$ T.

Alternatively, the deflection field generator may comprise an electrostatic field generator. This is preferably achieved by providing a transverse electrostatic field in the region of the exit opening/entrance port. A number of electrode configurations could be selected to provide such a field, but most simply a pair of electrically isolated parallel plates, preferably with equal and opposite potentials applied thereto, could be mounted respectively above and below the opening/port. As before, the sample still needs to be shielded from the deflection field and techniques known in the art can be used to achieve this. Preferably, however, the electron deflection field is provided magnetically.

Preferably, the X-ray generating means is arranged to produce monochromated primary X-rays. It is thereby possible to provide a highly focused beam of primary X-rays.

Advantageously, the analysis system may comprise a second electron deflection field generating means. The first and second electron deflection field generating means may then be placed at different locations within the system, selected from 1) in the entrance port of the side wall of the analysis chamber; 2) internally of the housing portion of the X-ray generating means; and 3) externally of the housing portion of the X-ray generating means. This may be advantageous where the chamber sidewall is relatively thin, so that the strength of a deflection field generating means located in the port would have to be correspondingly reduced. By providing a further electron deflection field generating means upstream of the port, for example, deflection of the unwanted electrons away from the sample surface may be more certain.

According to a further aspect of the invention, there is provided a method of X-ray photoelectron spectroscopy analysis by primary beam irradiation of a sample surface, the method comprising the steps of: generating at an X-ray generating means primary X-rays in a sample direction towards a sample surface; additionally generating at the X-ray generating means unwanted electrons which would travel in the sample direction towards the sample surface; and providing an electron deflection field upstream of the sample surface to deflect the unwanted electrons away from the sample direction, such that the unwanted electrons are prevented from reaching the sample surface.

Preferably the system(s) of the invention form part of a spectroscopic system for secondary particle emission surface analysis of a sample, also comprising an analysis chamber, a flood gun, and a secondary particle analyser.

According to a still further aspect of the invention, there is provided an X-ray photoelectron spectroscopy analysis system for surface analysis of an insulating sample, the system comprising: an analysis chamber for holding the sample, the chamber comprising a sidewall having a port therethrough; and an X-ray generation means arranged to supply X-rays through the port in the chamber for primary beam irradiation of the sample surface, wherein, in use, unwanted electrons are generated in the X-ray generation means and travel from the X-ray generation means towards the sample surface, the system further comprising and electron deflection field generating device located at, near to, or upstream of the port and arranged to deflect the unwanted electrons such that the unwanted electrons do not reach the sample surface.

Other preferred features and advantages of the invention are set out in the description and in the dependent claims which are appended hereto.

BRIEF DESCRIPTION OF THE DRAWINGS

The invention may be put into practice in a number of ways and some embodiments will now be described, by way of example only, with reference to the following figures, in which.

DESCRIPTION OF PREFERRED EMBODIMENTS

Figure 1:
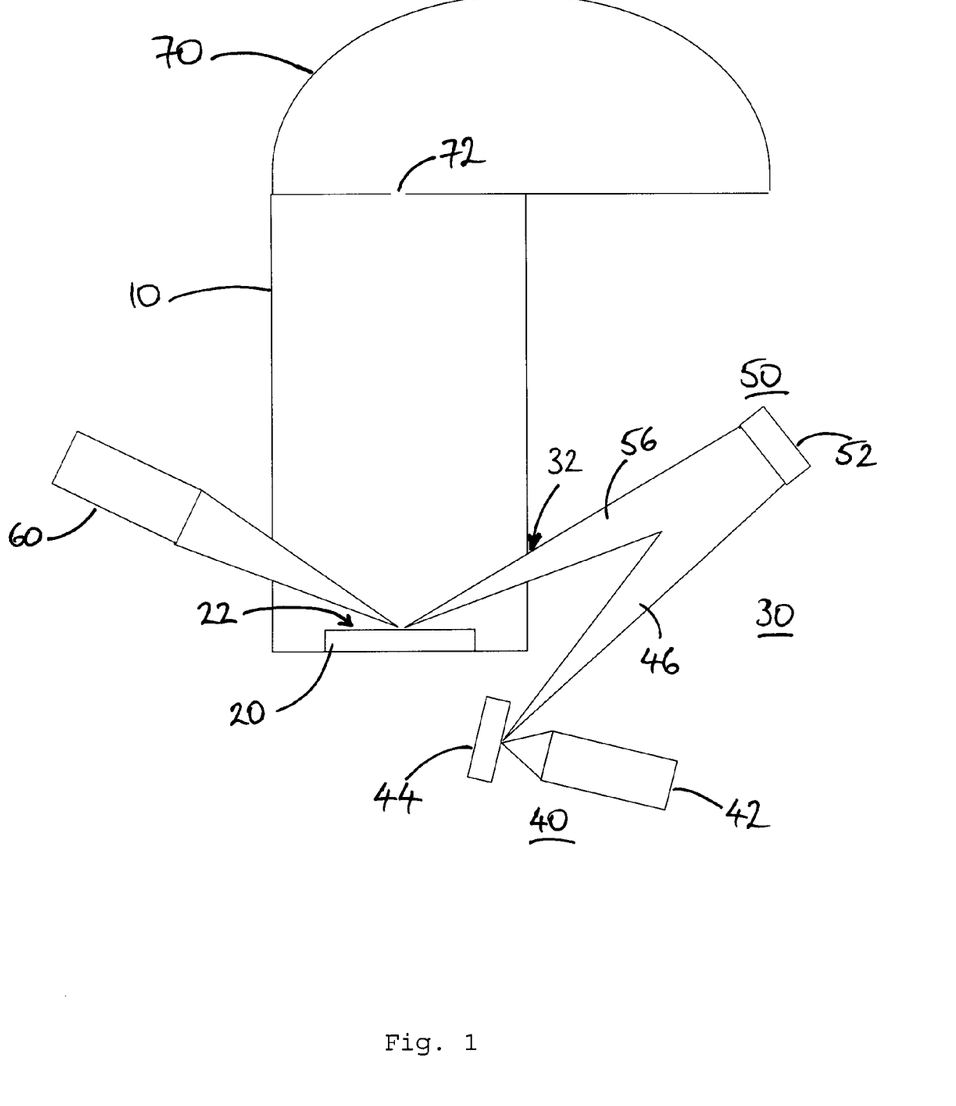
FIG. 1 shows, highly schematically, a general spectroscopic system for secondary particle emission surface analysis of a sample, to which the invention may be applied.

Referring to FIG. 1, a schematic spectroscopic system for secondary particle emission surface analysis of a sample is shown. The system includes an analysis chamber 10, which is typically a vacuum chamber capable of sustaining an ultra-high vacuum. The chamber 10 holds a sample 20, whose surface 22 is to be investigated for materials characterisation. In the embodiment shown, the system is set up for X-ray photoelectron spectroscopy. As such, the primary particle generator is an X-ray generator 30, which in this case is configured to produce monochromatic X-rays. The primary particle generator 30 comprises an X-ray source 40 and an X-ray monochromator 50. The X-ray source 40 is provided by a high-energy electron gun 42, which is arranged to accelerate electrons towards a target anode 44. The target anode 44 includes aluminium, so that electron bombardment of the target generates X-rays at the aluminium K-alpha wavelength. The resulting X-rays 46 travel from the X-ray source 40 towards a monochromator crystal 52. When the X-rays 46 strike the monochromator crystal 52, they are Bragg reflected as a monochromated beam of X-rays 56 and focused towards the sample surface 22. The monochromated X-rays 56 pass out of the primary particle generator 30 through an exit opening 32, into the analysis chamber 10.

As discussed above, for insulating samples, a flood gun 60 is employed to provide charge neutralisation at the sample surface 22, during analysis. The flood gun may be of any suitable type, but is preferably that disclosed in GB-A-2,411,763.

The monochromated X-ray photons cause the emission of secondary, photoelectrons from the sample surface 22. The photoelectrons are collected in the analysis chamber 10 and focused towards an analyser entrance opening 72, for energy analysis in a spectroscopic analyser/detector 70.

Figure 2:
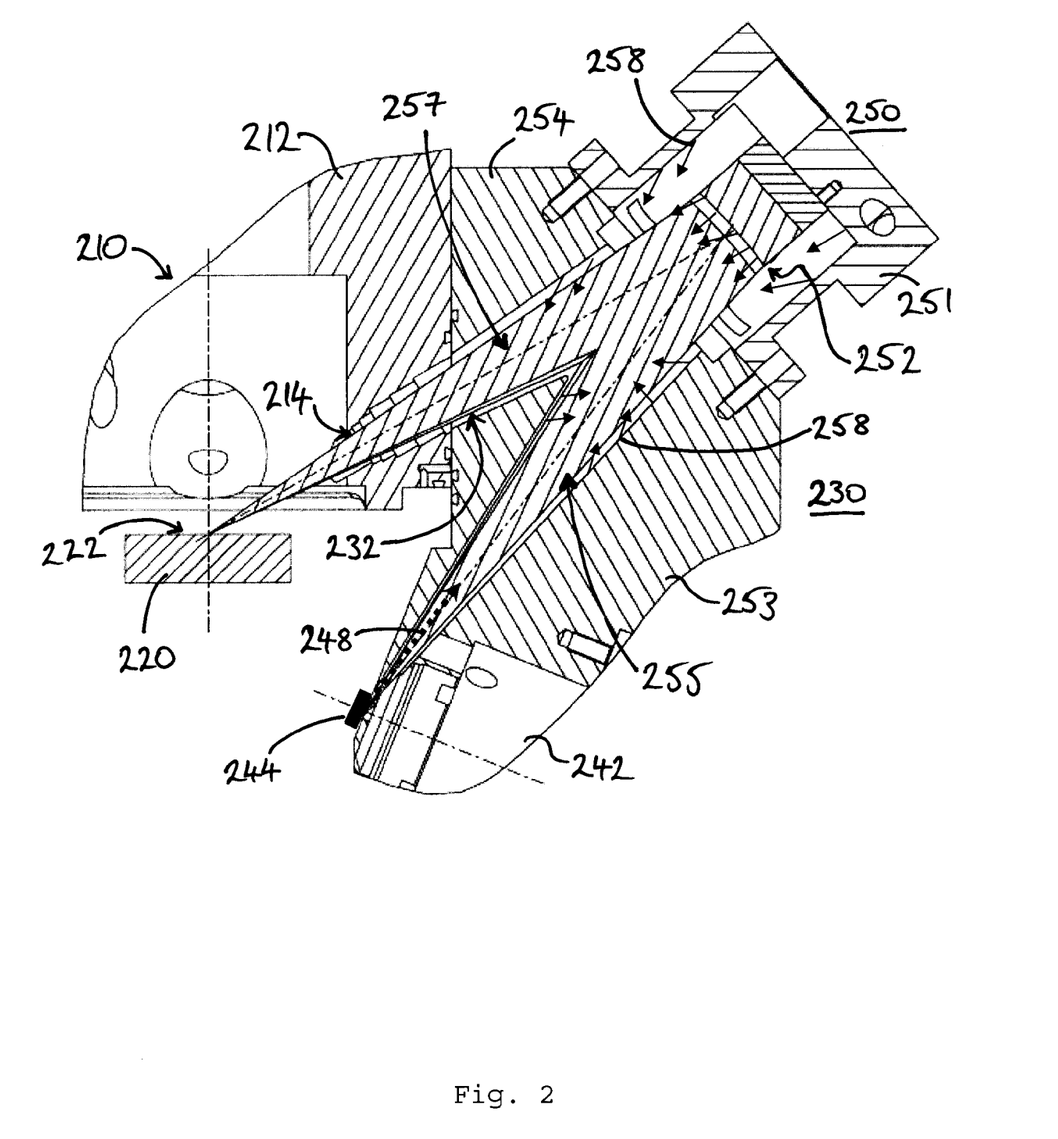
FIG. 2 shows a sectional view of part of an X-ray generator and an analysis chamber, illustrating the generation of unwanted electrons.

FIG. 2 shows a sectional view of a part of such a spectroscopic system. The part shown includes parts of a primary particle generator 230 and an analysis chamber 210. This figure illustrates the generation of unwanted electrons 248, 258.

FIG. 2 shows an electron gun 242 and target anode 244 in communication with an entrance arm or flight tube 255 to the monochromator 250. The entrance arm 255 leads to the monochromator crystal 252, which is held in place on a crystal mount 251. Downstream of the crystal 252 is an exit arm or flight tube 257 from the monochromator 250. The exit arm 257 terminates in an exit opening 232 to the primary particle generator 230. The entrance and exit arms 255, 257 are provided within entrance and exit housing portions 253, 254, respectively.

The monochromator housing portion 254 is fixed to a sidewall 212 of an analysis chamber 210. The sidewall 212 has an entrance port 214, which is in communication with the exit opening 232 of the primary particle generator 230. The entrance port 214 acts as an extension of the exit arm 257 of the primary particle generator 230 and is directed towards the sample surface 222 of a sample 220 held in the analysis chamber 210. In this way, primary X-rays generated by the primary particle generator 230 may pass out of the generator through the exit arm 257 and entrance port 214 and are focused towards an analysis region of the sample surface 222.

As well as producing primary X-rays at the target anode 244, the electron bombardment of the anode also results in the emission of high-energy secondary electrons from the anode. The emission of such secondary electrons is illustrated schematically by broken arrow 248. The high-energy electrons originating from the X-ray source 240 are scattered from the walls of the monochromator chamber (entrance and exit arms 255, 257), from the monochromator crystal 252 and from its mount 251. Stimulation of such surfaces by X-rays, either aluminium K-alpha X-rays or Bremsstrahlung X-rays, can lead to photoelectron emission. Direct electron bombardment of such surfaces by these electrons and by electrons originating from the X-ray source 240 can also result in the emission of secondary or higher-order electrons. The production of such unwanted electrons within the primary particle generator 230 is illustrated by exemplary arrows 258. At least a proportion of the unwanted electrons would pass out of the primary particle generator 230, through the exit opening 232 and entrance port 214, towards the sample surface 222, resulting in a build-up of undesirable negative charge on the sample surface.

Figure 3:
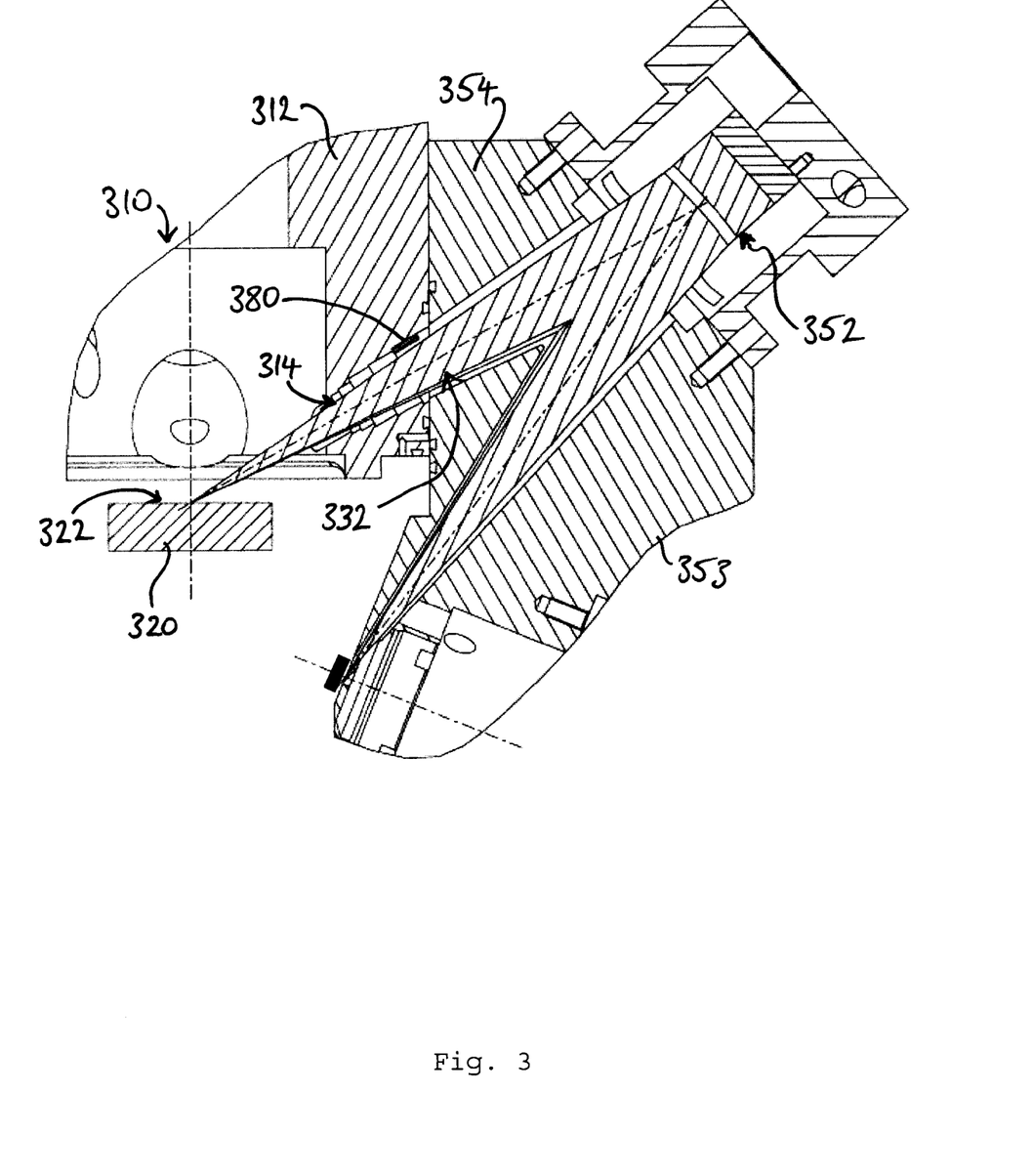
FIG. 3 shows a sectional view of part of an X-ray generator and an analysis chamber, with an electron deflection field generator in position.

FIG. 3 shows a similar sectional view to that of FIG. 2, but without the arrows showing the unwanted electron production. Accordingly, like features are referred to with like reference numerals (the initial digit corresponding to the number of the figure).

The embodiment of FIG. 3 incorporates an electron deflection field generator, in the form of a permanent magnet 380. The magnet 380 is positioned within the sidewall 312 of the analysis chamber 310, on an internal surface of the entrance port 314. The magnet 380 is positioned in a vertically upper region of the entrance port 314, adjacent an interface between the entrance port and the exit opening 332 of the primary particle generator 330. The location of the magnet 380 in FIG. 3 is the currently preferred position for the electron deflection field generator.

The chamber sidewall 312—at least that part surrounding the entrance port 314—is made of a magnetic material, such as soft iron or, preferably, a nickel-iron alloy. This serves a number of purposes. Firstly, the chamber sidewall 312 can be used to shield the sample surface magnetically from the magnetic field produced by the magnet 380. If the chamber sidewall 312 is sufficiently thick that the magnetic field produced by the magnet 380 does not saturate the material forming the sidewall and its shielding factor remains high, it is possible to achieve a magnetic field at the sample surface of less than $10^{-6}$ T, which is sufficiently low as to have a negligible effect on photoelectrons emitted from the sample surface. Secondly, the magnetic part of the sidewall 312 surrounding the entrance port 314 forms part of the magnetic circuit for the magnetic flux from the magnet 380.

Where the sidewall 312 is not required to have magnetic properties (i.e., away from the entrance port 314), the sidewall may be made of other material, including non-magnetic materials. For example, such other parts of the sidewall 312 may be made of stainless steel or an aluminium alloy.

With a magnetic material surrounding the entrance port 314, the magnet 380 may be positioned within the entrance port and held in place by magnetic attraction to the surface of the entrance port. If desired, additional mechanical mounting (which may include a machined recess in the surface of the entrance port) and fixings may be provided to hold the magnet 380 in place. Once the magnet is fitted in place within the entrance port 314, there is no further set-up required for its operation.

In this way, the magnet 380 is arranged in the entrance port 314 to provide a magnetic field which is essentially transverse to the direction of the unwanted electrons travelling towards the sample surface 322. The force on the unwanted electrons may accordingly be towards a maximum value for a given strength of magnetic field and speed of the unwanted electrons. The force on the unwanted electrons acts to deflect them to one side or the other, preferably into the surface of the entrance port 314 or other parts of the chamber sidewall 312 of the analysis chamber 310.

The magnetic field should be of sufficient strength to deflect the highest-energy unwanted electrons, such that they are prevented from reaching the sample surface 322 and instead hit the sidewall 312 of the chamber 310. Any low-energy unwanted electrons are forced to circulate in the magnetic field, until they also hit the surface of the entrance port 314 or other parts of the sidewall 312. The inventor has found that a magnetic field across the entrance port 314 of a few to tens of millitesla is sufficient to prevent the high-energy unwanted electrons from arriving at the sample surface 322. Accordingly, a magnetic flux density of between 1 mT and 100 mT is desirable. Preferably, however, the value is between 10 mT and 50 mT.

Thus, although the charge neutralisation technique disclosed in GB-A-2,411,763 provides an effective way of neutralising the unwanted electrons at the sample surface, the inventor has found that even better results may be obtained by removing the majority of the unwanted electrons before they reach the sample surface. Indeed, the unwanted electron current reaching the sample surface can be reduced by more than a factor of ten, using the above embodiment. A first benefit of this is that the positive ion beam generated by a charge neutralisation system employed with the analysis system (either as described by GB-A-2,411,763 or any other suitable means) can be correspondingly reduced in ion current, thereby reducing damage caused to the sample during analysis. A second benefit is that, because the positive ion beam current may be reduced, the amount of gas which is to be ionised to provide the ion beam (typically argon gas) which needs to be admitted to the charge neutralisation system and the analysis chamber may be significantly reduced. Accordingly, contamination of the analysis system may be reduced. A further benefit is that the performance of the charge neutralisation system may be enhanced by the improvement in ease of use, especially for large samples where the ion beam neutralisation techniques above have limited efficacy. In particular, the set-up of the flood gun is much easier. Once the flood gun has been initially aligned with the analysis region on the sample surface, it has been found that no further alignment is necessary to accommodate samples of varying size, shape, electrical properties, or surface texture. Furthermore, no adjustments have been found to be required when the spot size of the monochromated X-ray beam is varied.

Figure 4:
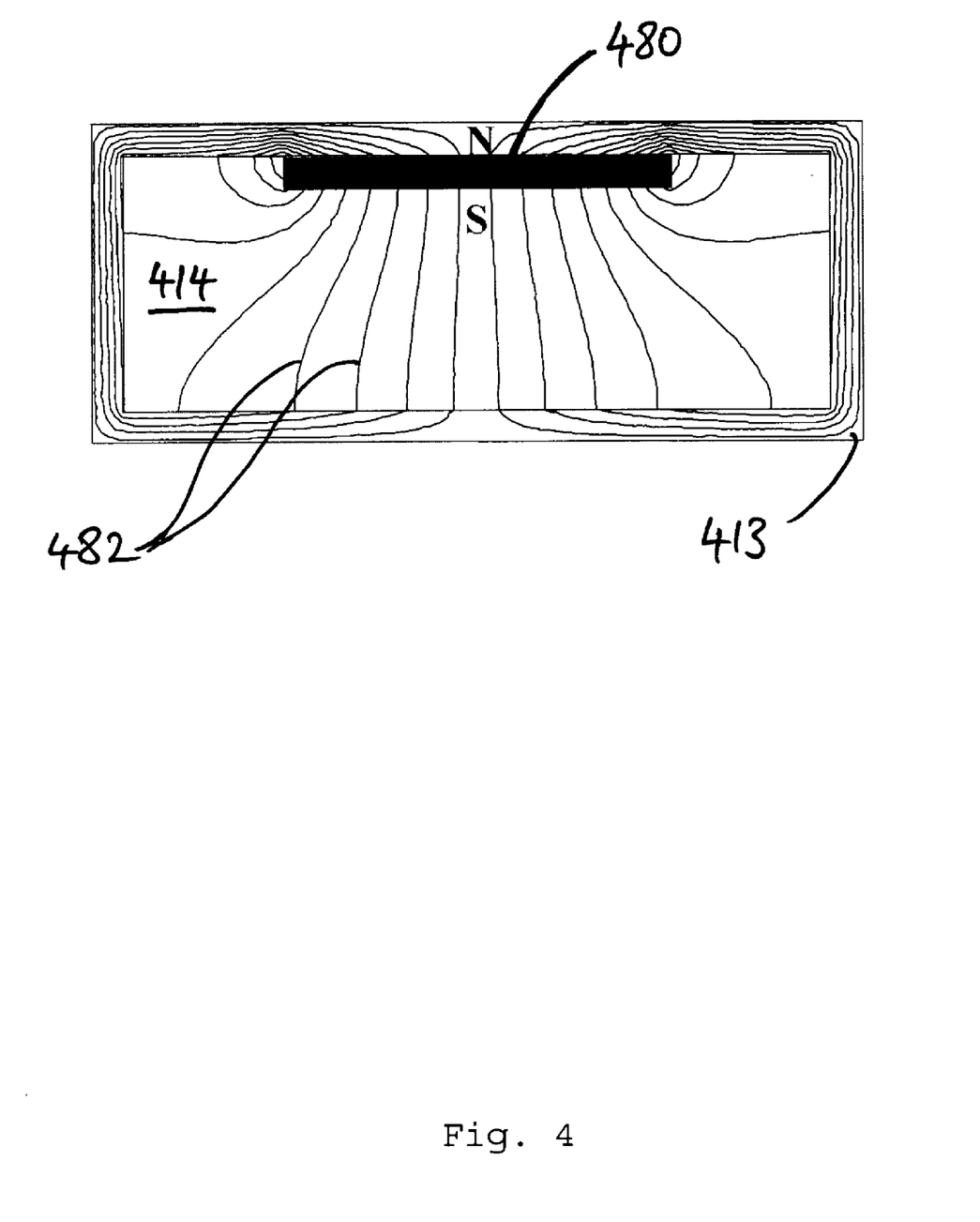
FIG. 4 shows, schematically, a sectional view of an entrance port to an analysis chamber with a permanent magnet in position.

FIG. 4 shows, schematically, a sectional view of an entrance port 414 to an analysis chamber (not shown). As discussed above, a part 413 of the sidewall of the chamber near the entrance port 414 is made of a magnetic material, in the preferred embodiment. A permanent magnet 480 is held in place to an inside surface of the entrance port 414, by magnetic attraction. The north pole of the magnet 480 faces the inside surface of the entrance port 414, to which the magnet is held. Magnetic flux lines 482 leave the north pole of the magnet 480 and are returned towards the south pole by the flux return path provided by the magnetic part 413 of the chamber sidewall. In this way, magnetic flux lines 482 run generally transversely across the entrance port 414. It will be appreciated that the polarity of the magnet is not important, since this will merely affect whether the unwanted electrons are deflected to one side or the other.

In the currently preferred embodiment, the entrance port in the chamber sidewall is rectangular, with dimensions of approximately 20 mm by 100 mm. Also, the magnet preferably has dimensions (length, width, depth) of 60 mm by 12 mm by 2.5 mm, with the direction of magnetisation substantially normal to the large faces of the magnet. The chamber sidewall forming the flux return path preferably has a thickness of about 40 mm at this point. However, although these dimensions are currently preferred, they are not critical to the operation of the invention and other suitable configurations are envisaged.

The magnet used in this embodiment is a permanent magnet. Preferably, the permanent magnet used is bakeable without losing its magnetisation. Generally, surface analysis systems operate in ultra-high vacuum conditions. Such UHV systems are routinely baked to temperatures of 100° C. or greater, in order to achieve pressures below around $10^{-8}$ torr. If the magnet cannot be baked to such temperatures without demagnetising, then it would need to be removed for bake-out. This is clearly not possible if the magnet is to be located inside the vacuum region and still extremely inconvenient even if the magnet is mounted outside of the vacuum region. A high-temperature grade of neodymium iron boron or of samarium cobalt has been found to be suitable.

Figure 5:
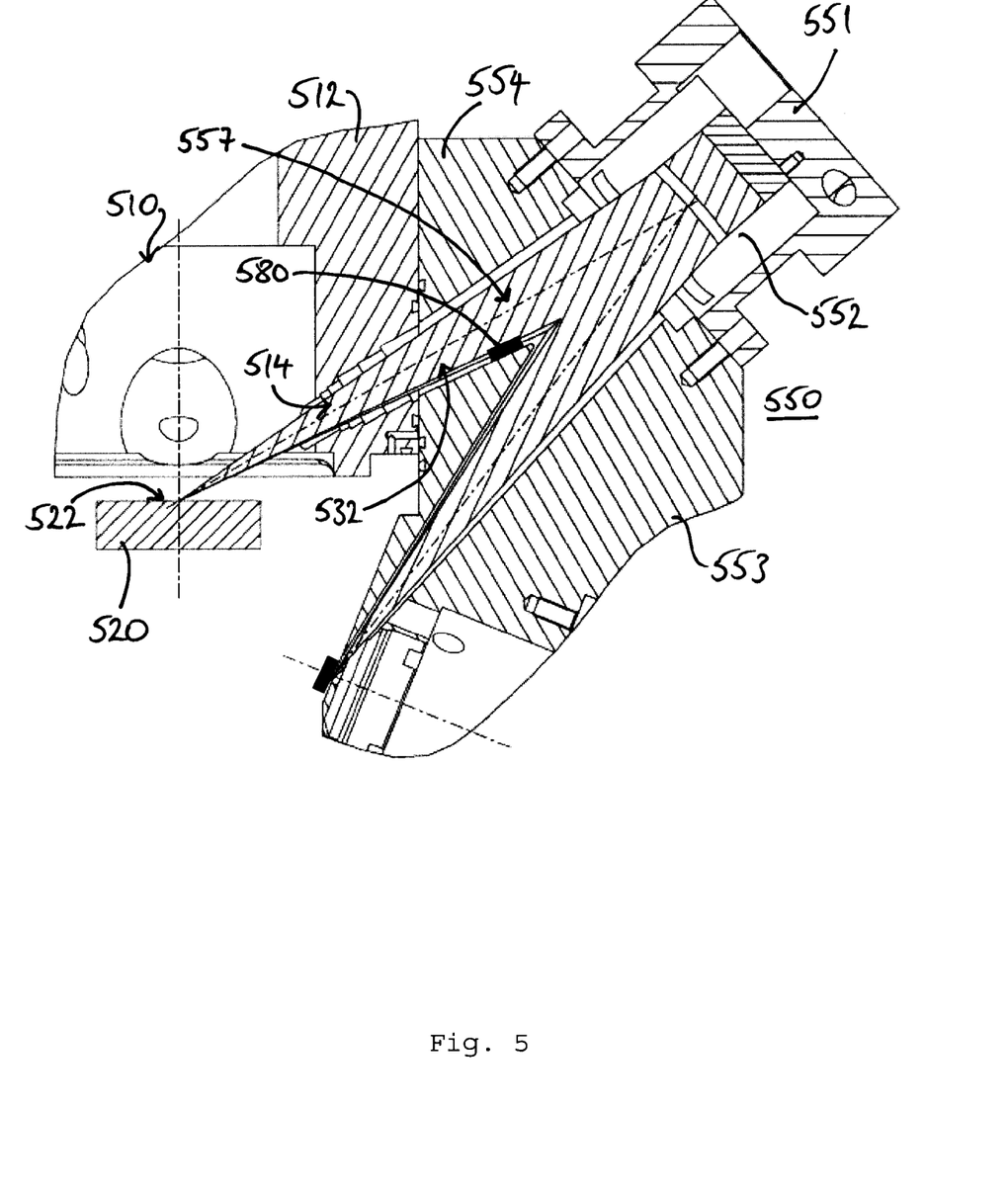
FIG. 5 shows a sectional view of part of an X-ray generator and an analysis chamber, with an electron deflection field generating means in an alternative position.

FIG. 5 shows a sectional view of part of an X-ray generator and an analysis chamber, illustrating an embodiment with the electron deflection field generating means in an alternative position. In the embodiment shown, the electron deflection field generator is a permanent magnet 580. The magnet 580 is located outside of the analysis chamber 510 and is fixed to an inside surface of the exit arm 557 to the X-ray monochromator 550. The monochromator housing portions 553, 554 are not made from a magnetic material, to avoid interfering with the electrons generated by the electron gun of the X-ray source. Accordingly, the magnet 580 is held in place using mechanical fixings, which may include a machined recess, spring clips, screws etc., as will be readily understood.

The magnet 580 is configured to provide a magnetic field substantially transverse to the direction of the unwanted electrons heading towards the exit opening 532 of the primary particle generator 530. Thus, in the same way as before, the electrons are deflected by the magnetic field to one side or the other. Preferably, the deflected unwanted electrons are absorbed by the surfaces of the exit arm 557 and entrance port 514 but, in any case, are prevented from reaching the sample surface 522.

In the embodiment shown, with the magnet 580 external to the chamber sidewall, no dedicated flux return path has been employed. While not essential, it would nevertheless be beneficial to use a flux return path, machined as a separate magnetic component and disposed around the exit arm 557 at the location of the magnet 580.

The alternative position for the magnet 580, shown in FIG. 5, may be beneficial where the chamber sidewall 512 of the analysis chamber 510 is not thick enough to provide adequate magnetic shielding to the sample 520 with the magnet 580 being positioned closer to, or within, the sidewall.

In an alternative embodiment, the magnet is positioned outside of the vacuum region (i.e. not within the exit arm 557 or the entrance port 514). The magnet could be located outside of the monochromator housing portion 554, or in a suitable recess within the housing portion (but not inside the exit arm 557 itself), such that its magnetic field penetrates through the non-magnetic housing portion and into the exit arm 557 and/or part of the entrance port 514, to deflect the unwanted electrons. In general, this embodiment would result in a lower field strength within the exit arm 557 or entrance port 514, for a given magnet, but might be advantageous if the magnet is provided by an electromagnet, or if a high bake-out temperature for the system necessitates the removal of a permanent magnet during bake-out.

As will be understood from the above embodiments, the electron deflection field generator is arranged to deflect unwanted electrons away from their path towards a sample surface upstream of the sample. The inventor has found it is preferable for a magnet to be positioned within the chamber sidewall or outside of the chamber sidewall (for example, internally of the entrance port, internally of the exit arm to the X-ray generator, or externally of the exit arm to the X-ray generator), so as to reduce or minimise the introduction of any magnetic field inside the analysis chamber.

The inventor has found that an effective location for the magnet is just outside the chamber sidewall, either internally or externally of the exit arm of the X-ray monochromator. However, the inventor has established that the optimum position for the magnet is within the chamber sidewall, on the surface of the entrance port, using the chamber sidewall itself as a magnetic flux return path. Placing the magnet near to the entrance port in this way has the benefit that the beam passing through the entrance port (the beam containing unwanted electrons) is relatively narrow, so that the volume through which the magnetic field needs to act is relatively small.

In the above embodiments, the magnet used to provide the electron deflection field is a permanent magnet. However, in some embodiments, it may be desirable to employ an electromagnet to provide the electron deflection field. In this case, the configuration and function of the electromagnet would be the same as for the embodiments using a permanent magnet. However, when an electromagnet is used, it is preferable for the electromagnet to be mounted externally of the analysis chamber and externally of the exit arm to the X-ray monochromator.

The use of a magnetic field to deflect charged particles, by means of either a permanent magnet or an electromagnet, is known. For example, U.S. Pat. No. 5,204,530 discloses a noise reduction technique for negative-ion quadrupole mass spectrometry. A weak magnetic field is supplied between a quadrupole mass spectrometer and an ion collector/detector. A beam passes through the quadrupole and enters the magnetic field, where electrons are deflected away from the beam path to an electron collector and the negative ions pass undeflected to the ion collector where they are detected and recorded as a mass spectrum. However, to the knowledge of the inventor, the surface-charging problem in XPS, caused by relatively high-energy unwanted electrons from an X-ray monochromator has not previously been recognised. The inventor believes that the technique of the present invention is considered to be a significant improvement in the field of XPS.

Although the above embodiments employ a magnet as the electron deflection field generator, an electrostatic field generator could alternatively be used. Such an arrangement could employ an electrostatic field of sufficient strength to deflect the electrons away from their path towards the sample surface, so that they impinge upon the walls of the analysis chamber, its entrance port, or the exit arm of the monochromator. Alternatively, the electrostatic field could be employed to repel the unwanted electrons completely, so that they do not pass further downstream of the electrostatic field. In order to deflect the unwanted electrons, preferably a transverse electrostatic field is created in the region of the exit opening of the primary X-ray generator or the entrance port to the analysis chamber. A number of electrode configurations may be chosen to provide this electrostatic field, as will be understood readily, but most simply a pair of electrically isolated parallel plates could be mounted above and below the opening/port. Preferably the plates would be arranged to have equal and opposite potentials applied to them, for providing the transverse electrostatic field.

The electrostatic field required to deflect or stop the high-energy electrons from the X-ray generator is relatively large and is reasonably difficult to generate in a way which does not physically obstruct the X-ray beam passing towards the sample, or produce stray electrostatic fields which interfere with the secondary particle analysis. Given such mechanical design considerations, the preferred embodiment of the invention involves the use of a permanent magnet, as described above.

In the embodiments described above, a single electron deflection field generator has been employed. However, in some embodiments, it may be advantageous to provide a second electron deflection field generator. This may be so, for example, if the strength of a single electron deflection field is required to be below a certain level, so as not to interfere with the analysis of secondary particles in the analysis chamber. Providing two electron deflection fields at separate locations may provide greater certainty of unwanted electron deflection. The first magnetic or electrostatic field may be applied 1) in the entrance port of the sidewall of the analysis chamber; 2) internally of the housing portion of the X-ray generator; or 3) externally of the housing portion of the X-ray generator. The second electron deflection field may then be applied at another of the above regions.

The invention claimed is:

1. A system comprising an X-ray photoelectron spectroscopy analysis apparatus configured to analyze an insulating sample, the apparatus including:
an X-ray generating means having an exit opening and being arranged to generate primary X-rays which pass out of the exit opening in a sample direction towards a sample surface for irradiation thereof, the X-ray generating means in use additionally generating unwanted electrons which would pass out of the exit opening substantially in the sample direction;

an electron deflection field generating means arranged to generate a deflection field upstream of the sample surface, the deflection field being configured to deflect the unwanted electrons away from the sample direction, such that the unwanted electrons are prevented from reaching the sample surface, and a flood gun for charge neutralization of the sample surface.

2. The system of claim 1, wherein the deflection field generating means is located near to, at, or upstream of the exit opening.

3. The system of claim 1, wherein the deflection field generating means is arranged to generate the deflection field transverse to the sample direction.

4. The system of claim 1, wherein the X-ray generating means has a housing portion terminating in the exit opening and the deflection field generating means is located internally of the housing portion.

5. The system of claim 1, wherein the X-ray generating means has a housing portion terminating in the exit opening and the deflection field generating means is located externally of the housing portion.

6. The system of claim 1, further comprising an analysis chamber for holding the sample, the chamber comprising a sidewall having an entrance port therethrough, the port being in communication with the exit opening of the X-ray generating means for passage of the generated X-rays towards the sample surface, wherein the deflection field generating means is located in the port.

7. The system of claim 1, wherein the deflection field generating means comprises a magnet arranged to produce a local magnetic field of between 1 mT and 100 mT.

8. The system of claim 1, wherein the deflection field generating means comprises a magnet arranged to produce a local magnetic field of between 10 mT and 50 mT.

9. The system of claim 6, wherein the deflection field generating means comprises a magnet and at least a part of the chamber sidewall surrounding the entrance port is made of a magnetic material and is configured to act as a flux return for the deflection field generating means.

10. The system of claim 6, wherein the deflection field generating means comprises a magnet and at least a part of the chamber sidewall surrounding the entrance port is made of a magnetic material and is configured to provide magnetic shielding for the sample surface, such that a magnetic field at the sample surface is less than $10^{-6}$ T.

11. The system of claim 1, wherein the X-ray generating means is arranged to produce monochromated primary X-rays.

12. The system of claim 1, further comprising a second electron deflection field generating means, the second electron deflection field generating means occupying a different location from the first electron deflection field generating means.

13. An X-ray photoelectron spectroscopy analysis system for secondary particle emission surface analysis of an insulating sample, comprising:

the system of any of claims 1 to 12;

an analysis chamber for holding the sample; and a secondary particle analyser for receiving and analysing secondary particles emitted from the sample surface.

14. A method of X-ray photoelectron spectroscopy analysis by primary beam irradiation of a sample surface, the method comprising:

generating at an X-ray generating means primary X-rays in a sample direction towards a sample surface of an insulating sample;

additionally generating at the X-ray generating means unwanted electrons which would travel in the sample direction towards the sample surface;

providing an electron deflection field upstream of the sample surface to deflect the unwanted electrons away from the sample direction, such that the unwanted electrons are prevented from reaching the sample surface; and neutralizing charging of the sample surface using a flood gun.

15. The method of claim 14, wherein the X-ray generating means has an exit opening through which the X-rays pass and the electron deflection field is generated in the region of the exit opening.

16. The method of claim 14, wherein the electron deflection field is transverse to the sample direction.

17. The method of claim 15, wherein the X-ray generating means has a housing portion terminating at the exit opening and the electron deflection field is generated internally of the housing portion.

18. The method of claim 15, wherein the X-ray generating means has a housing portion terminating at the exit opening and the electron deflection field is generated externally of the housing portion.

19. The method of claim 14, wherein the X-ray generating means is in communication with an analysis chamber for holding the sample, the chamber comprising a sidewall having an entrance port therethrough for passage of the X-rays towards the sample surface, wherein the electron deflection field is generated in the port.

20. The method of claim 14, wherein the electron deflection field comprises a magnetic electron deflection field and produces a local magnetic field of between 1 mT and 100 mT.

21. The method of claim 14, wherein the electron deflection field comprises a magnetic electron deflection field and produces a local magnetic field of between 10 mT and 50 mT.

22. The method of claim 19, wherein the electron deflection field is a magnetic electron deflection field, further comprising the step of using a part of the chamber sidewall surrounding the entrance port, the part being made of a magnetic material, to act as a flux return path for the electron deflection field.

23. The method of claim 14, wherein the electron deflection field is a magnetic electron deflection field, further comprising the step of magnetically shielding the sample surface, such that a magnetic field at the sample surface is less than $10^{31\ 6}$ T.

24. The method of claim 14, wherein the X-rays produced by the X-ray generating means are monochromated X-rays.

* * * * *